US006603021B2

(12) United States Patent
Werpy et al.

(10) Patent No.: US 6,603,021 B2
(45) Date of Patent: Aug. 5, 2003

(54) METHODS OF MAKING PYRROLIDONES

(75) Inventors: Todd Werpy, West Richland, WA (US);
John G. Frye, Jr., Richland, WA (US);
Yong Wang, Richland, WA (US); Alan H. Zacher, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/884,602

(22) Filed: Jun. 18, 2001

(65) Prior Publication Data

US 2003/0097006 A1 May 22, 2003

(51) Int. Cl.$^7$ .......................................... C07D 207/267
(52) U.S. Cl. ...................................... 548/552
(58) Field of Search ......................... 548/552

(56) References Cited

U.S. PATENT DOCUMENTS

| | | | |
|---|---|---|---|
| 2,267,757 A | 12/1941 | Schuster et al. | |
| 2,674,602 A | 4/1954 | Schuster | |
| 3,080,377 A | 3/1963 | Liao | 260/326.5 |
| 3,092,638 A | 6/1963 | Liao et al. | 260/326.5 |
| 3,109,005 A | 10/1963 | Lidov | |
| 3,198,808 A | 8/1965 | Walldorf et al. | 260/326.5 |
| 3,448,118 A | 6/1969 | Chichery et al. | 260/326.5 |
| 3,634,346 A | 1/1972 | McKeon et al. | |
| 3,637,743 A | 1/1972 | Prince | |
| 3,661,894 A | 5/1972 | Wehner et al. | |
| 3,681,387 A | 8/1972 | Hollstein et al. | 260/326.5 |
| 3,767,644 A | 10/1973 | Fukuoka et al. | |
| 3,775,431 A | 11/1973 | Rodewald | |
| 3,812,148 A | 5/1974 | Hollstein et al. | 260/326.5 |
| 3,884,936 A | 5/1975 | Hollstein | |
| 3,966,763 A | 6/1976 | Greene | |
| 4,012,418 A | 3/1977 | Schaafsma et al. | |
| 4,151,171 A | 4/1979 | Kurkov | |
| 4,152,331 A | 5/1979 | Meijer et al. | |
| 4,263,175 A | 4/1981 | Pesa et al. | 252/473 |
| 4,404,391 A | 9/1983 | Meyer et al. | |
| 4,420,620 A | 12/1983 | Murib | |
| 4,731,454 A | 3/1988 | Otake et al. | 548/543 |
| 4,780,547 A | 10/1988 | zur Hausen et al. | 548/552 |
| 4,814,464 A | 3/1989 | Olsen | 548/552 |
| 4,841,069 A | 6/1989 | Olsen | 548/545 |
| 4,851,546 A | 7/1989 | Graham et al. | |
| 4,885,371 A | 12/1989 | Tracy et al. | |
| 4,904,804 A | 2/1990 | Matson | |
| 5,101,044 A | 3/1992 | Schuster et al. | |
| 5,101,045 A | 3/1992 | Koehler et al. | 548/554 |
| 5,106,730 A | 4/1992 | Van Ness et al. | |
| 5,157,127 A | 10/1992 | Weyer et al. | 548/552 |
| 5,276,165 A | 1/1994 | Weyer et al. | |
| 5,338,861 A | 8/1994 | Botta et al. | |
| 5,347,021 A | 9/1994 | Taylor et al. | |
| 5,401,856 A | 3/1995 | Grey et al. | |
| 5,434,273 A | 7/1995 | Weyer et al. | 548/554 |
| 5,478,950 A | 12/1995 | Bergfeld et al. | |
| 5,508,396 A | 4/1996 | Steffen | |
| 5,536,849 A | 7/1996 | Bergfeld et al. | |
| 5,847,213 A | 12/1998 | Karusu et al. | |
| 5,912,358 A | 6/1999 | Frohn et al. | |
| 6,008,375 A | 12/1999 | Bergfeld et al. | |
| 6,075,153 A | 6/2000 | Bergfeld et al. | |
| 6,248,902 B1 | 6/2001 | Bertola | |
| 6,348,601 B2 | 2/2002 | Ohlbach et al. | |
| 6,350,883 B1 | 2/2002 | Chen et al. | |
| 6,429,316 B1 | 8/2002 | Takahashi et al. | |

FOREIGN PATENT DOCUMENTS

| | | |
|---|---|---|
| CH | CN1104635 | 7/1995 |
| CH | CN1173492 | 2/1998 |
| CZ | CS146054 | 11/1972 |
| CZ | CS191496 | 7/1979 |
| CZ | CS212181 | 2/1982 |
| DE | 2025172 | 1/1971 |
| DE | 2165643 | 7/1972 |
| DE | 3701297 | 7/1988 |
| DE | 19626123 | 1/1998 |
| EP | 0027022 | 4/1981 |
| EP | 0252242 | 1/1988 |
| EP | 0460474 | 12/1991 |
| EP | 0464359 | 1/1992 |
| EP | 0545150 | 6/1993 |
| EP | 632030 | 1/1995 |
| EP | 0745589 | 12/1996 |
| EP | 1201652 | 5/2002 |
| FR | 1439192 | 5/1966 |
| JP | 42023344 | 11/1967 |
| JP | 47018751 | 5/1972 |
| JP | 47021420 | 6/1972 |
| JP | 47027975 | 10/1972 |
| JP | 49000259 | 1/1974 |
| JP | 49020582 | 5/1974 |
| JP | 49020585 | 5/1974 |
| JP | 49020586 | 5/1974 |
| JP | 49048432 | 12/1974 |
| JP | 51016657 | 2/1976 |
| JP | 51042107 | 11/1976 |

(List continued on next page.)

OTHER PUBLICATIONS

Cerveny et al CAS Abstract 125:141930, (1996), 61(5), 764–769.*

Nghiem et al., "An integrated process for the production of chemicals from biologically derived succinic acid", ACS Symposium Series, 2001, vol. 748, pp. 160–173. (abstract only).

(List continued on next page.)

Primary Examiner—Joseph K. McKane
Assistant Examiner—Kamal Saeed
(74) Attorney, Agent, or Firm—Wells St. John P.S.

(57) ABSTRACT

The present invention provides methods for making N-methylpyrrolidine and analogous compounds via hydrogenation. Novel catalysts for this process, and novel conditions/yields are also described. Other process improvements may include extraction and hydrolysis steps. Some preferred reactions take place in the aqueous phase. Starting materials for making N-methylpyrrolidine may include succinic acid, N-methylsuccinimide, and their analogs.

27 Claims, 2 Drawing Sheets

FOREIGN PATENT DOCUMENTS

| | | |
|---|---|---|
| JP | 62120360 | 6/1987 |
| JP | 63027476 | 2/1988 |
| JP | 01186863 | 7/1989 |
| JP | 01190667 | 7/1989 |
| JP | 011868864 | 7/1989 |
| JP | 03081261 | 4/1991 |
| JP | 10158238 | 6/1998 |
| JP | 11349566 | 12/1999 |
| JP | 2000256312 | 9/2000 |
| JP | 2001002638 | 1/2001 |
| JP | 2001002640 | 1/2001 |
| JP | 2001114760 | 4/2001 |
| JP | 2001302626 | 10/2001 |
| JP | 2001354646 | 12/2001 |
| JP | 2001354647 | 12/2001 |
| RO | 96953 | 5/1989 |
| RO | 111189 | 7/1996 |
| RO | 113640 | 9/1998 |
| RU | SU259889 | 12/1969 |
| RU | SU619484 | 8/1978 |
| RU | SU1558903 | 4/1990 |
| RU | SU1735283 | 5/1992 |
| RU | SU1735284 | 5/1992 |
| WO | WO2001030755 | 5/2001 |

OTHER PUBLICATIONS

Subba Rao et al., "Synthesis of five-membered heterocycles over modified ZSM-5 catalysts", Catalysis: Modern Trends, Dec. 1994, pp. 110–113. (abstract only).

Miyajima, "Manufacturing process for N–methyl pyrrolidone", Chem. Econ. Eng. Rev., 1971, vol. 3(10), pp. 29–31. (abstract only)(Year is sufficiently early so that the month is not in issue).

Castiglioni et al., "Gamma–Butyrolactone for production of solvents with low environmental impact", Chimica e l'Industria (Milan), 1996, vol. 78(5), pp. 575–581. (abstract only)(Year is sufficiently early so that the month is not in issue).

Ershler et al., "Electroreduction of n–Methylsuccinimide to N–methylpyrrolidone", Elektrokhimiya 1979, vol. 15(4), pp. 520–526. (abstract only)(Year is sufficiently early so that the month is not in issue).

Yu et al., "Production and application of N–methyl–2–pyrrolidone", Henan Huagong, 1999, vol. 7, pp. 10–12. (abstract only)(Year is sufficiently early so that the month is not in issue).

Takahata et al., "N–Alkylation of lactams with phase transfer catalyst", Heterocycles, 1979, vol. 12(11), pp. 1449–1451. (abstract only)(Year is sufficiently early so that the month is not in issue).

Auerbach et al., "N–Methylation of amides, lactams, and ureas", Journal Org. Chem., 1976, vol. 41(4), pp. 725–726. (abstract only)(Year is sufficiently early so that the month is not in issue).

Subba Rao et al., "Modified ZSM–5 Catalysts for the Synthesis of Five and Six–Membered Heterocyclic Compounds", Journal of Organic Chemistry, 1994, vol. 59(14), pp. 3998–4000. (abstract only)(Year is sufficiently early so that the month is not in issue).

Kukalenko et al., "New synthesis of N–aryl and N–alkylpyrrolidones, and some of their properties"Khim. Geterotsikl, Soedin., 1971, vol. 7(6), pp. 773–774. (absteact only)(Year is sufficiently early so that the month is not in issue).

Anonymous, "Process for the isomerization of 4–methylamino–2–buten–1–Ol to N–methylpyrrolidinone", Research Disclosure, 1993. (abstract only)(Year is sufficiently early so that the month is not in issue).

Sojka et al., "Problems in preparation of 2–pyrrolidinone and N–methylpyrrolidinone", Ropa a Uhlie, 1985, pp. 400–410. (abstract only)(Year is sufficiently early so that the month is not in issue).

Xue et al., "Studies on N–methyl–alpha–pyrrolidone synthesis", hanghai Huagong, 1996, pp. 10–14. (abstract only) (Year is sufficiently early so that the month is not in issue).

Qiu et al., "Synthesis of N–methyl–2–pyrrolidone in vapor phase in the presence of catalysts" Shiyou Huagong, 1996, pp. 179–182. (abstract only)(Year is sufficiently early so that the month is not in issue).

Yan, "Preparation of 1–methyl–2–pyrrolidone by electrochemical method", Tianranqi Huagong, 2000, pp. 44–46. (abstract only)(Year is sufficiently early so that the month is not in issue).

Yano, "N–methyl–2–pyrrolidone", Yuki Gosei Kagaku Kyokaishi, 1983, pp. 880–881. (abstract only)(Year is sufficiently early so that the month is not in issue).

Cen et al., "N–alkylation of amides, imides, and lactams under phase–transfer catalysis", Zhongguo Yiyao Gongye Zazhi, 1990, pp. 218–220. (abstract only)(Year is sufficiently early so that the month is not in issue).

* cited by examiner

H₄NO₂CCH₂CH₂COONH₄ + H₂ diammonium succinate + hydrogen gas catalyst / CH₃OH; catalyst = Pd/ZrO₂/C 2-pyrolidone         N-methylpyrolidone

METHODS OF MAKING PYRROLIDONES

STATEMENT OF GOVERNMENT RIGHTS

This invention was made with Government support under contract DE-AC0676RLO 1830 awarded by the U.S. Department of Energy. The Government has certain rights in this invention.

FIELD OF THE INVENTION

The present invention relates to methods of making pyrrolidones, especially N-methyl pyrrolidone ("NMP"), by hydrogenation.

BACKGROUND OF THE INVENTION

Olsen, in U.S. Pat. No. 4,841,069 described reactions of succinic anhydride, methanol and hydrogen. In Example 1, Olsen described a reaction in which 67 g of succinic anhydride, 62 g of methanol, and 12.53 g of ammonia were heated 5 hrs in an autoclave at 300° C. with stirring. Olsen reported that 100% of the succinic anhydride was converted with a selectivity to N-methylsuccinimide ("NMS") of 90%. In Example 11, Olsen described a reaction in which 65 g of succinic anhydride, 41 g of methanol, and 12.15 g of ammonia, 12 g of 5% palladium on carbon catalyst, and 700 psig of hydrogen were heated 21. hrs at 290° C. with stirring. Olsen reported that 100% of the succinic anhydride was converted with a 60% selectivity to N-methylsuccinimide and a 30% selectivity to N-methylpyrrolidone.

Olsen, in U.S. Pat. No. 4,814,464 (which is very similar to U.S. Pat. No. 4,841,069), described the same or similar ammonolysis-alkylation reactions in which a succinic derivative such as the anhydride, acid or diester is reacted with ammonia and a $C_1$ to $C_4$ alkanol and converted to an N-alkylsuccinimide. Olsen stated that "In general, the reactants, substrate, ammonia, and alkanol, are used in about stiochiometric proportions. Too little ammonia or alkanol results in incomplete conversion, and too much ammonia is wasteful and produces undesirable by-products." However, Olsen also states that "preferably excess of the alcohol is used." It is reported that products can be separated by distillation or crystallization. See Col. 3, lines 50–59.

Olsen also remarked that the N-alkylsuccinimide can be reduced catalytically with hydrogen either continuously or batchwise. In Example 1, Olsen reported hydrogenating NMS at 230 C. for 2 hours over a nickel catalyst to yield a 60% NMS conversion with an 89% selectivity to NMP. In Example 3, Olsen reported reacting 73 g dimethylsuccinate, 37 g ammonium hydroxide, 12 g of 5% palladium on carbon catalyst, and 700 psig of hydrogen for 21 hrs at 290 C. with stirring. Olsen reported that 1 00% of the dimethylsuccinate was converted with a 70% selectivity to N-methylsuccinimide and a 20% selectivity to N-methylpyrrolidone.

Koehler et al., in U.S. Pat. No. 5,101,045, described a process for the preparation of N-substituted pyrrolidones by catalytic hydrogenation of maleic anhydride, maleic acid and/or fumaric acid in the presence of ammonia, a primary alcohol and a modified cobalt oxide catalyst. In Example 3, Koehler et al. stated that 75 ml of a 45% aqueous diammonium maleate solution and 75 ml methanol were hydrogenated for 42 hours at 230 C. in the presence of 10 g of a modified cobalt oxide catalyst. Koehler et al. reported that the product contained 89 mol % NMP, 5.0 mol % pyrrolidine and methylpyrrolidine, and 2.7 mol % of succinimide and methylsuccinimide.

Liao, in U.S. Pat. No. 3,092,638, and Hollstein et al., in U.S. Pat. No. 3,681,387, described hydrogenating succinimide. Hollstein et al. run the hydrogenation in water over a palladium on carbon catalyst.

Liao, in U.S. Pat. No. 3,080,377, Himmele et al., in U.S. Pat. No. 3,198.808. Hollstein et al., in U.S. Pat. No. 3,681,387, and Pesa et al. in U.S. Pat. No. 4,263,175 described hydrogenating succinic acid or succinic anhydride in the presence of ammonia to yield 2-pyrrolidone. Catalysts used include: palladium on carbon, ruthenium on carbon, ruthenium on alumina, and cobalt oxide. Himmele et al. stated that an ammonium salt can be used in place of ammonia.

Chichery et al., in U.S. Pat. No. 3,448,118, and Weyer et al. in U.S. Pat. Nos. 5,157,127 and 5,434,273, disclosed methods of making N-substituted pyrrolidones in which succinic anhydride, succinic acid, or the like is hydrogenated in the presence of a primary amine. Chichery et al. run their hydrogenations in water with a palladium on charcoal catalyst. Weyer et al. used a modified cobalt oxide catalyst.

zur Hausen et al., in U.S. Pat. No. 4,780,547, described hydrogenation of NMS over a nickel catalyst. In Example 2, zur Hausen et al. stated that comparable results can be obtained using succinic anhydride and methylamine in place of NMS.

SUMMARY OF THE INVENTION

The invention provides methods of making a compound having the formula:

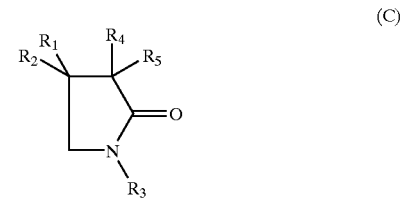

(C)

wherein $R_1$, $R_2$, $R_4$, and $R_5$ are, independently, H or a $C_1$ to $C_6$ alkyl or substituted alkyl; and $R_3$ is H or a $C_1$ to $C_6$ alkyl or substituted alkyl. These methods involve hydrogenation.

In a first aspect, a composition containing a compound having the formula:

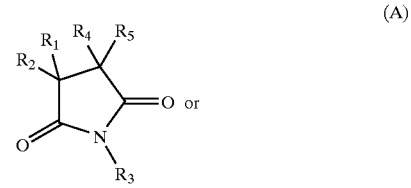

(A)

or

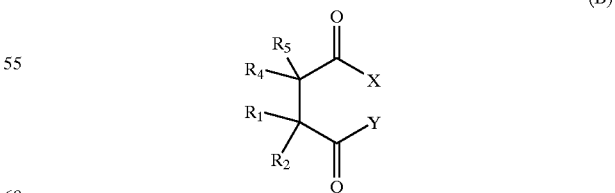

(B)

wherein $R_1$, $R_2$, $R_4$, and $R_5$ are, independently, H or a $C_1$ to $C_6$ alkyl or substituted alkyl; or wherein $R_2$ and $R_4$ together are replaced by a double bond; $R_3$ is H or a $C_1$ to $C_6$ alkyl or substituted alkyl; and X and Y are, independently, OH, O⁻, or where X and Y together are a bridging oxo; is reacted with hydrogen, in the presence of water and a catalyst.

Preferably, the catalyst includes carbon, metal oxide and at least one metal selected from Pd, Rh, Pt, Ru, Ni or Co. In some embodiments, a compound of formula (A) is purified prior to hydrogenation. Thus, in some embodiments, a compound of formula (C) is made in a process having at least 3 steps. In a first step, a compound of formula (B) is reacted with an ammonia source, in the presence of water, to form a compound having formula (A). Then, in a second step, the compound of formula (A) is extracted into an organic solvent. In a third step, the compound of formula (A), that was extracted in the second step, is hydrogenated in the presence of a catalyst.

It has also been surprisingly discovered that, in some processes, the yields of compound (C) can be increased substantially by hydrolyzing compositions formed during hydrogenation reactions of compounds (A) and/or (B). A portion of the composition formed by hydrogenating (A) and/or (B) can be hydrolyzed (i.e., reacted with water) to produce a compound or compounds of formula (C); this portion is referred to as a compound (C) precursor. To prevent over-reduction (and lower yields), the compound (C) precursor is separated from hydrogen, the hydrogenation catalyst, or both hydrogen and the catalyst.

In another aspect, the invention provides a method of making a compound of formula (C), in which a composition including a compound having the formula:

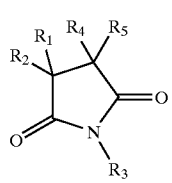

(A)

wherein $R_1$, $R_2$, $R_4$, and $R_5$ are, independently, H or a $C_1$ to $C_6$ alkyl or substituted alkyl; and $R_3$ is H or a $C_1$ to $C_6$ alkyl or substituted alkyl; is reacted with and hydrogen in the presence of a Pd, Rh, Pt, Ru, Ni or Co catalyst; at a temperature of less than 220° C. and for a time of less than 10 hours. In this method, compound (C) is obtained in a yield of at least 80%.

Advantages of various embodiments of the present invention include: higher yields, better purity, more stable catalysts, lower reaction temperatures, shorter reaction times, and lower costs. Unexpectedly superior results were discovered under various conditions, including: using a metal oxide (such as zirconia) textured catalyst; hydrogenating a succinimide below 220° C. for less than ten hours; and hydrogenating aqueous phase compositions having a relatively high concentration of compound (B).

For fermentation or other biologically-derived compositions, it is desirable to separate out proteins and other contaminants, prior to the hydrogenation to produce compound (C). For example, proteins in these compositions could poison a hydrogenation catalyst. Thus, there may be important advantages in separating out an imide, such as compound A, and hydrogenating the extracted imide. An extraction step prior to the formation of N-methylpyrrolidine can produce unexpectedly superior results, especially for biologically-derived starting materials.

DESCRIPTION OF THE PREFERRED EMBODIMENT(S)

Figure 1:
FIG. 1 illustrates a one-step reaction of diammonium succinate to 2-pyrrolidone and NMP.
Figure 1:

Reactants in the inventive process include the compounds (A) and (B) described above. Preferably, $R_1$, $R_2$, $R_4$, and $R_5$ are H or a lower alkyl, preferably methyl, ethyl or propyl, more preferably $R_1$, $R_2$, $R_4$, and $R_5$ are all H. X and Y can be the same or different and preferably are OH or O$^-$ (such as in an ionic oxygen species such as O$^-$[NH$_4$]$^+$). In some preferred embodiments, X and Y together are a single bridging oxygen an anhydride such as succinic anhydride. Typically, X and Y are in an equilbrium such as between OH and anhydride or between O$^-$[NH$_4$]$^+$ and OH+NH$_3$. $R_3$ is preferably H or a lower alkyl, preferably methyl, ethyl or propyl; most preferably, $R_3$ is methyl.

The reactants may come from a variety of sources. For example, succinic acid can be produced in situ from hydrogenation of maleic acid. In some preferred embodiments, the reactant composition is derived from fermentation or other biological process and will typically be in an aqueous solution or mixture (also referred to as an aqueous composition or aqueous phase composition).

When it is desirable to convert a compound of formula B (which for the purposes of this disclosure can be called a "succinate"), the reaction mixture must contain an ammonia source, most typically ammonia or ammonium. The ammonia source can be added, such as by adding gaseous or aqueous ammonia, or can be present in the succinate feedstock, such as aqueous diammonium succinate. Preferably, ammonia (including ammonium) is present in a range of 1 to 3 molar ratio of ammonia to succinate, more preferably 1 to 2. Ammonia can be present in the feedstock or added before or during the reaction. The succinate is preferably in aqueous solution, preferably having a concentration of 5 to 60 weight %, more preferably 15 to 30 wt. %. The reaction mixture preferably contains an alcohol, R$_3$OH where $R_3$ is a C, to $C_6$ alkyl or substituted alkyl, preferably methanol. The alcohol may be formed in situ, but is preferably added to the reaction mixture as an alcohol. It has been found that the reaction is sensitive to alcohol content, with higher alcohol content leading to higher yields of the N-alkylated product such as NMP. Preferably, the alcohol is present in a ratio (alcohol compound B) of at least about 2:1. The reaction preferably occurs in water.

The reactant (A) can be hydrogenated in solution or neat. In preferred embodiments, the reactant (A) is obtained from compound (B) and purified before hydrogenation. In many cases, the purified compound (A) may convert to product in greater yield and with fewer side products than an unpurified mixture. Most preferably, (A) is N-methyl-succinimide (NMS).

The product pyrrolidone, compound (C), preferably has the same $R_1$–$R_5$ as in the reactant compound or compounds. In some preferred embodiments, the product is N-methyl pyrrolidone (NMP).

Formation of product (C) from compounds (A) or (B) requires hydrogenation over a hydrogenation catalyst. Preferably the catalyst contains Rh, Pd, Pt, Ru, Ni or Co which are active metals for this hydrogenation. More preferably, catalyst also contains Re, such as in Pd-Re or Rh-Re. The hydrogenation catalyst typically includes a porous support material. Supports selected in the present invention are preferably selected to be stable in the reactor environment in which they are intended for use. Preferably, the supports are hydrothermally-stable, meaning that the support loses less than 15 % of its surface area after 72 hours in water at 150° C. More preferably, the support is hydrothermally-stable such that it loses less than 5% of its surface area after 72 hours in water at 150° C. Preferred support materials include porous carbon and rutile. An especially preferred support is a porous, high surface area activated carbon, such as carbons with CTC values around 120%, available from Calgon and Engelhard. For good dispersion of the catalytic sites, the support preferably has a high surface area and a pore volume of 10 to 98%, more preferably 30 to 90%.

In preferred embodiments, a metal oxide is disposed on the porous support. Preferably, for aqueous phase applications, the oxide contains at least one of Zr, Ti, Hf, Ta, Nb, Mo, and W. Preferably, the metal oxide contains at least 50%, more preferably at least 90%, by mass of an oxide or oxides of one or more of Zr, Ti, Hf, Ta, Nb, Mo, and W. In some embodiments, the metal oxide is substantially completely composed of an oxide or oxides of one or more of Zr, Ti, Hf, Mo, and W. The rutile form of titania is especially preferred. In alternative embodiments, oxides of other elements such as Si, Al, Zn, Sn, V, Fe, U, Th, etc. may be used. The metal oxide is preferably present in 1 to 25 weight %, more preferably 5 to 10 weight percent of the total weight of the dried catalyst. Typically, the metal of the metal oxide is fully oxidized (for example $TiO_2$, $ZrO_2$, etc.) with terminal or bridging oxides; however, in less preferred embodiments the oxide could contain, in addition to oxygen, hydrogen in hydroxyls (which may be difficult to differentiate from hydrated oxides), sufides, cations, oxygen-containing anions, and the like. The catalyst metal (such as Pd, Rh, etc. including combinations of catalyst metals) is preferably present in 0.1 to 10 weight %, more preferably 2.5 to 5.0 weight percent of the total weight of the dried catalyst.

In some preferred embodiments, the catalyst is characterized by one or more of the following characteristics: a minimum, smallest dimension of at least about 100 $\mu$m, more preferably at least about 300 $\mu$m; at least 70%, more preferably at least 80% of the catalyst component is within about 5 $\mu$m, more preferably about 2 $\mu$m, of 80% of the minimum area of the metal oxide. Preferably, at least about 5%, more preferably at least about 10%, of the catalyst component, and at least about 5%, more preferably at least about 10%, of the metal oxide is disposed in pores that are at least about 10 $\mu$m, more preferably at least about 20 $\mu$m, away from the exterior of the support. The foregoing properties are conducted by cutting a catalyst particle or monolith to obtain a cross-section of at least about 100 $\mu$m in both height and width. The metal oxide is then imaged by an elemental analysis spectroscopic technique, and the minimum area that encompasses 80% of the metal oxide is then identified. This area (or areas) is then increased by a 5 (or 2) $\mu$m margin around each area or areas. Then, the distribution of catalyst in the cross-sectional area is imaged by an elemental analysis spectroscopic technique; at least 70% of the catalyst component is within the area of the 80% of metal oxide (including the margin). Amounts of each element is quantified by intensity. It is not necessary that all cross-sections exhibit the characteristics described herein, but, for a desired catalyst, at least some cross-section has these characteristics. Preferably, the 80% of the metal oxide plus 5 $\mu$m margin occupies less than 90%, more preferably less than 40%, of the total cross-sectional area. The converse preferably also occurs, that is, at least 70%, more preferably at least 80%, of the metal oxide is within the minimum area of 80% of the catalyst component plus a 5 (or 2) $\mu$m margin around each area or areas.

Preferably, at least about 50% of the catalyst component is within about 10 $\mu$m of the exterior of the support. In some embodiments, some internal pores have at least 2 times, and in some cases at least 3 times, as much of the catalyst component as compared with the metal oxide. In preferred embodiments, the majority, more preferably at least about 80%, of catalyst component, and/or the metal oxide, that is located within the interior of the support (that is, that portion of the catalyst component and/or metal oxide which is at least about 10 $\mu$m from the exterior of the support) is located in pores having at least one dimension of at least about 5 $\mu$m. The foregoing values are measured based on SEM analysis of cross-sections of catalysts.

Some preferred embodiments of the inventive catalysts may, alternatively, be described with reference to the method by which the catalyst is made. Alternatively, some preferred embodiments of the invention can be described by reactivities. For example, in some preferred embodiments, the catalyst exhibits a succinic acid conversion of at least 50% after 5 hours under the conditions set forth in Table 1.

Catalysts are preferably made by solution/colloid techniques. A porous support may be purchased or prepared by known methods. A metal oxide sol is prepared or obtained. A sol may be prepared, for example, by dissolving a metal compound and adding water or changing pH to form a sol. Each of the oligomeric or colloidal particles in the sol contain a metal and oxygen; these particles may also contain other components such as halides, cations, etc. The sol could be prepared, for example, by dissolving a metal alkoxide, halide, etc. in an anhydrous solvent, then adding sufficient water to form a sol. In some preferred embodiments, organic solvents are avoided and the sol is prepared only in water. Conditions for preparing sols will depend on the type of metal and available ligands. In some preferred embodiments, the sol is prepared at between about 10 and about 50° C. In some preferred embodiments, in aqueous solutions, the sol is preferably formed at a pH of between 1 and 6, more preferably between 2 and 5. The metal oxide precursor sol is contacted with the porous support. This could be done, for example, by dipping the support in the sol or colloid, or dispersing the sol in a volume of solvent equivalent to the incipient wetness of the support, so that the solvent exactly fills the void fraction of the catalyst upon contacting and is dried to deposit the metal oxide on the surface of the support. In the case of a particulate support, such as activated carbon powders, the support and metal oxide precursor composition can be mixed in a suspension. The porous support is preferably not coated by a vapor-deposited layer, more preferably the method of making the catalyst does not have any vapor deposition step. The catalyst component can be deposited subsequent to, or simultaneous with, the deposition of the metal oxide. The catalyst component can be impregnated into the support in a single-step, or by multi-step impregnation processes. In a preferred method, the precursor for the catalyst component is prepared in a sol that is deposited after, or codeposited with, the metal oxide precursor sol. In some preferred embodiments, the precursor for the catalyst component is prepared under the same conditions as the metal oxide precursor sol, for example as an aqueous colloidal mixture in the desired pH range. After the metal oxide and catalyst component have been deposited, the catalyst is typically dried. Also, following deposition, if desired, the catalyst component can be activated by an appropriate technique such as reduction under a hydrogen-containing atmosphere.

The inventive reactions can be accomplished in a one-step (A or B to C) or a two-step reaction (B to C). In some preferred embodiments, B is converted to A in a continuous process, and the resulting compound A is hydrogenated in a batch or continuous process. Preferably, A is purified prior to hydrogenation.

One example of a one-step reaction is illustrated in FIG. 1. A succinate, such as 20 weight % aqueous diammonium succinate, is hydrogenated in aqueous methanol at 265° C. and 1900 psi $H_2$ to produce 2-pyrrolidone (hereinafter referred to as "2-py," which is also known as 2-pyrrolidinone) and N-methylpyrrolidone. This route is conducted as a one step process; however, it has been found that the reaction proceeds though an N-methylsuccinimide intermediate. 2-py and NMP are obtained in a 90% yield based on the diammonium succinate starting material. The ratio NMP:2-py is about 2:1.

Figure 2:
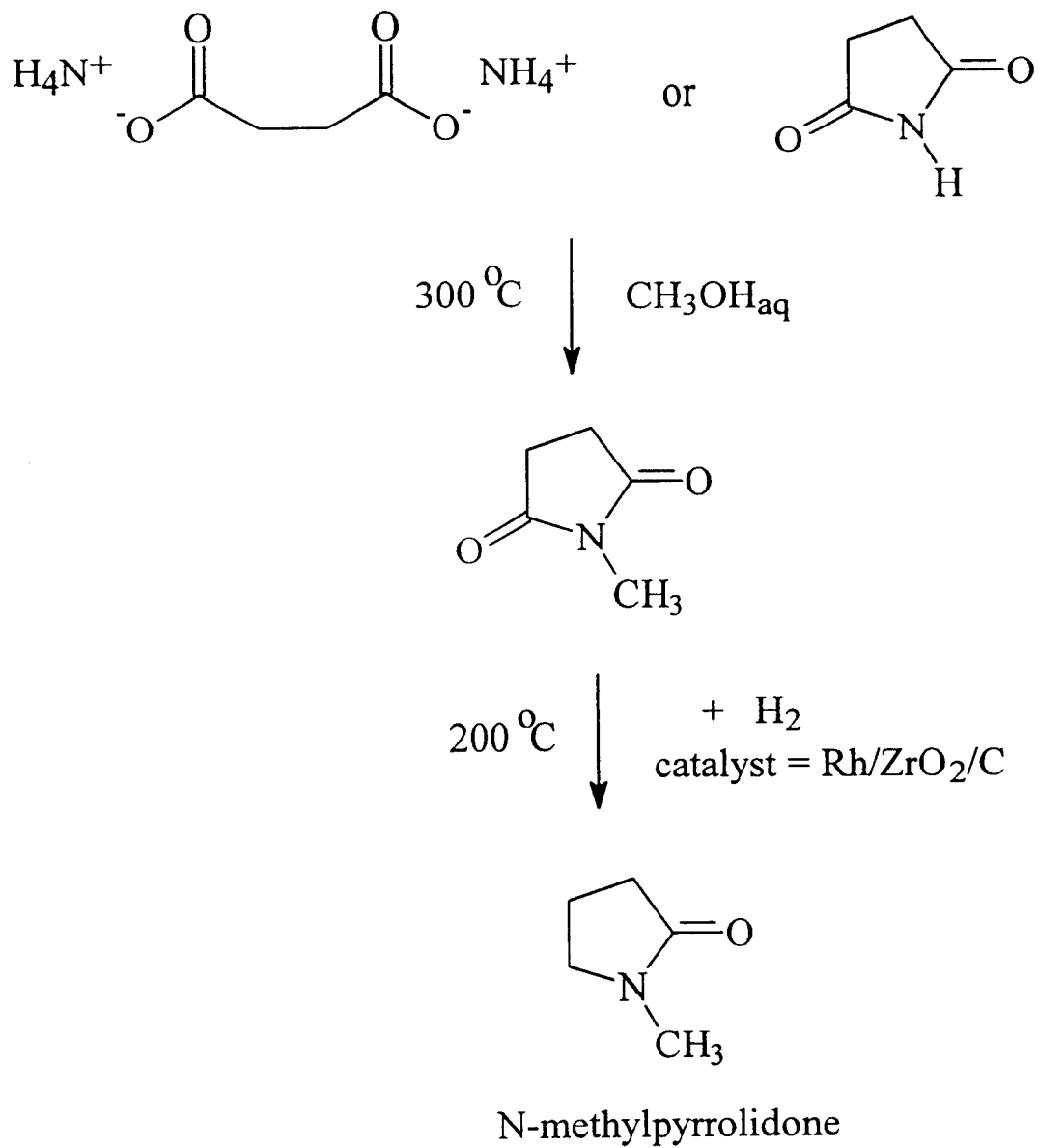
FIG. 2 illustrates a two-step reaction of diammonium succinate or succinimide to NMP.

An example of a two-step reaction is illustrated in FIG. 2. In the first step of this route, a succinate, such as 20 weight % aqueous diammonium succinate or succinimide, is reacted with methanol at about 300° C. to produce N-methylsuccinimide. The first step does not require a catalyst. In the second step, aqueous N-methylsuccinimide is hydrogenated at 200° C. and 1900 psi $H_2$ for about 8 hours to produce NMP. The hydrogenation is conducted over a catalyst of $Rh/ZrO_2/C$ or Rh-Re/C. Following hydrogenation, NMP can be isolated by distillation. If residues are present, the non-distilled residue is subjected to hydrolysis.

In some preferred embodiments, the succinimide produced in the first step is extracted into an organic solvent. Extraction solvents may include alkanes (such as hexane), toluene, etc., and preferred extraction solvents include ethers and halocarbons. It has been found that chloroform is an excellent extraction solvent. Extractions can be conducted batchwise or in a continuous process.

For the one step reaction, temperature is preferably in the range of 200 to 350° C., more preferably 230 to 280° C. For the two-step reaction, better results are obtained if the second step is conducted at a lower temperature than the first step. The first step, which may be conducted in the absence of a catalyst, is preferably conducted at 250 to 350° C., more preferably 280 to 320° C. The second step, which requires a hydrogenation catalyst, has been found to yield better results if conducted at relatively low temperature, preferably at less than 230° C., more preferably at 180 to 220° C., and still more preferably 190 to 210° C.

Another important variable is time. As is well-known shorter reaction times are more economical and thus highly desirable. Preferably, reaction time for the one step process is less than about 24 hours, more preferably about 4 to about 10 hours. In the two-step process, reaction time for the first step is less than about 4 hours, more preferably less than about 0.5 hours. In some embodiments, time for the first step is about 0.2 to about 2.5 hours, preferably less than 1 hour. Reaction time for the second step is preferably less than about 24 hours, more preferably less than one hour, and in some embodiments about 10 minutes to about 10 hours, more preferably 10 to 30 minutes. In some preferred embodiments, the hydrogenation can be described as a function of time and mass of catalyst; preferably at least one half gram of reactant (preferably NMS) hour per gram catalyst, i.e., at least (0.5 g reactant converted)(h)/(g catalyst). Alternatively, the hydrogenation preferably occurs at a rate of at least (20 g reactant converted)(h)/(g catalyst metal).

Hydrogenation is preferably conducted at a pressure of 600–1800 psi, more preferably 1000–1400 psi.

The reactions can occur in any reactor suitable for use under the desired conditions of temperature, pressure, and solvent. Examples of suitable apparatus include: trickle bed, bubble column reactors, and continuous stirred tank.

It has been discovered that methods of the present invention can produce surprisingly high yields at selected conditions and reaction times. In preferred embodiments of the one step reaction, product C (preferably NMP) is obtained in a yield of at least 70%, more preferably at least 80%, in some preferred embodiments, NMP and 2-py are obtained in greater than 90% yield and an NMP/2-py ratio of at least 2.0. Yield of NMS is preferably at least 70% to about 90%, more preferably at least 80%. Conversion of NMS to NMP in methods of the present invention are preferably at least 70% to about 90%, more preferably at least 80%, with NMP/2-py ratio of at least 5, more preferably at least 50. Yields are measured by gas chromatography. The product can be purified by known procedures such as distillation or extraction.

In some preferred embodiments, at least a portion of the product composition obtained from a hydrogenation reaction is hydrolyzed and either recovered or recycled back into a reactor. The yield of pyrrolidones diminishes at long reaction times in the presence of hydrogen and a hydrogenation catalyst—this may be due to over-reduction of products. Therefore, the hydrolysis process is preferably conducted by removing the presence of either the hydrogen or the catalyst or both.

Hydrogenation of compounds (A) and/or (B) may result in a product composition containing compound (C) and a compound (C) precursor composition, where hydrolysis of the precursor composition yields additional compound (C). Following removal of hydrogen and/or hydrogenation catalyst, any portion of the product composition could be hydrolyzed. For example, the product composition could be hydrolyzed as a continuous stream. The hydrolysis reaction could also be accomplished, for example, by a packing the second half of a continuous flow reactor with an inert heat transfer packing so that following the conversion of an aqueous feedstock to a liquid product composition, the liquid composition could remain at hydrolysis reaction conditions outside of the presence of catalyst. Additionally, a secondary inert packed reactor could follow the primary reactor and gas/liquid separator to remove the hydrogen, and the secondary reactor could be operated at any desirable temperature and pressure combination that would result in the highest yield of product. Alternatively, compound (C) could be recovered, for example by distillation, from the product composition and the undistilled composition hydrolyzed to produce additional compound (C). Since higher yields of compound (C) precursor composition may result from lower temperature hydrogenation, in some embodiments, hydrogenation is conducted at below 200° C., in some embodiments the hydrogenation is conducted in the range of 150–200° C. The composition to be hydrolyzed preferably contains at least 20% by weight water, more preferably at least 50 wt. % water. Hydrolysis preferably is conducted at above 200° C., in some embodiments, in the range of 200–300° C. In some embodiments, hydrolysis is conducted for 2 to 15 hours.

EXAMPLES

Catalyst Preparation Examples

All catalysts prepared in the following examples were prepared on 20×50 mesh Engelhard 712A-5–1589-1 coconut shell carbon granules (nominal CTC number ~95%). Liquid holding capacity of the Engelhard carbon was determined to be ~0.76 cc/g (determined using the method of incipient wetness using D.I. water). A commercially prepared $Rh(NO_3)_3$ solution (10.37% Rh by wt.) was used as the source of Rh for the Rh-containing catalyst.

5% Rh/C Catalyst 16.0071 g of the carbon granules were weighed into a 2 oz wide mouth glass jar, then the jar containing the carbon was capped and set aside until needed. The liquid holding capacity of the 16.0071 g of carbon was calculated as 12.2 cc. The required wt. of Rh needed was calculated as follows:

[(16.0071 g C÷0.95)−16.0071 g]=0.84 g Rh required

The amount of the above $Rh(NO_3)_3$ solution was calculated as follows:

0.84 g Rh needed÷0.1037=8.12 g of the $Rh(NO_3)_3$ solution.

8.13 g of the $Rh(NO_3)_3$ solution (10.37% Rh by wt.) was weighed into an empty 25 ml graduated cylinder. Additional DI water was added so that the total solution volume was 12.2 ml (total solution wt.=13.9635 g). The contents of the graduated cylinder were then well mixed to insure homogeneity. The 12.2 cc of the above prepared $Rh(NO_3)_3$ solution was added dropwise (in ~0.8 ml increments) to the 16.0071 g of carbon granules that had been previously weighed out. The jar was recapped following each ~0.8 ml addition of solution and shaken vigorously to insure uniform wetting of the carbon. After all of the solution had been added to the jar containing the carbon, the jar was allowed to stand for an additional ~30 minutes to allow the solution to completely soak into the pores of the carbon. After standing for the ~30 minute period, the contents were again shaken vigorously to insure uniformity. The cap was then removed and placed in a vacuum oven to dry overnight (oven temperature =100° C.; under house vacuum). 2.5% Rh/2.5% Zr/C Catalyst 15.99 g of the carbon granules were weighed into a 2 oz wide mouth glass jar, then the jar containing the carbon was capped and set aside until needed. $ZrO(NO_3)_2 \cdot xH_2O$ (anhydrous FW =231.23 g/mole) was used as the source of Zr for this catalyst. 3.37 g of DI water and 0.41 g of 70% $HNO_3$ solution were added to a 25 ml graduated cylinder. Next, 1.0741 g of $ZrO(NO_3)_2 \cdot xH_2O$ was added to the graduate and the mixture heated on a hotplate until all of the $ZrO(NO_3)_2 \cdot xH_2O$ was dissolved. 4.09 g of the Rh(NO3)3 solution (10.37% Rh by wt.) was added to the graduate along with enough DI water to bring the total solution volume up to 12.2 cc. The contents of the graduated cylinder were then well mixed to insure homogeneity. The 12.2 cc of the above prepared Rh and Zr containing solution was added dropwise (in ~0.8 ml increments) to the carbon granules that had been previously weighed out. The jar was recapped following each ~0.8 ml addition of solution and shaken vigorously to insure uniform wetting of the carbon. After all of the solution had been added to the jar containing the carbon, the jar was allowed to stand for an additional ~30 minutes to allow the solution to completely soak into the pores of the carbon. After standing for the ~30 minute period, the contents were again shaken vigorously to insure uniformity. The cap was then removed and placed in a vacuum oven to dry overnight (oven temperature=100° C.; under house vacuum).

2.5% Rh/2.5% Re/C Catalyst 16.00 g of the carbon granules were weighed into a 2 oz wide mouth glass jar. A commercially available perrhenic acid solution (54.5% Re by wt.) was used as the source of the Re for this catalyst. 0.778 g of perrhenic acid solution (54.5% Re by wt.) and 4.0666 g of $Rh(NO_3)_3$ solution (10.37% Rh by wt.) were weighed into a 25 ml graduated cylinder and enough DI water added to bring the total solution volume up to 12.2 cc. The 12.2 cc of Rh and Re containing solution was first well mixed to insure homogeneity, then added dropwise, in 0.8 ml increments, to the jar containing the 16.00 g of carbon. The jar was recapped and shaken vigorously after each liquid addition. After all of the liquid had been added, the jar was allowed to stand capped for an additional 30 minutes to allow the liquid to soak into the pores of the carbon. After standing, the jar and its contents were again shaken vigorously to thoroughly mix the contents. The cap was then removed, and the open jar and its contents placed in a vacuum oven to dry overnight (oven temperature=100° C.; under house vacuum). The dried catalyst was loaded into the reaction chamber and reduced in situ.

Semi-Batch Reactor Run Examples

Table 1 contains a summary of semi-batch reactor run results showing how the choice of catalyst, feedstock, and process conditions can affect reaction rates and product selectivities in the liquid phase synthesis of pyrrolidinones. The first 11 entries in the table are representative of hydrogenation reactions involving aqueous phase feedstocks. The entries in Table__are representative of hydrogenation reactions of feedstock materials performed in non-aqueous solvents. The description of the preparation of the feedstock solutions, the catalyst pretreatment process, and the semi-batch reactor run procedures are described below. Table 2 contains a summary of semi-batch reactor results showing how the choice of feedstock and process conditions can affect the reaction rates and product yields in the non-catalytic, hydrothermal synthesis of N-methylsuccinimide.

Preparation of Aqueous Feedstock Solutions used in Semi-Batch Run Examples

Aqueous Feedstock Solution #1

244.18 g (2.068 moles) of succinic acid was weighed into a ½ gallon poly bottle. Next, 583.76 g (32.400 moles) of DI water was also added to the bottle. The contents of the bottle were then gently agitated to try to break up lumps of solid succinic acid, and to try to wet all of the solid. Next, 239.17 g (4.142 moles $NH_3$ & 9.360 moles $H_2O$) of concentrated ammonia solution (29.5% $NH_3$ by wt.) was added to the slurried mixture in the bottle. The bottle, containing the succinic acid/ammonia mixture, was then recapped to prevent the loss of material. The capped bottle was again agitated to enhance the mixing of the reactants. The bottle warmed to ~50° C. due to the neutralization reaction, and was cooled down to room temperature by holding the bottle under cold, running water for several minutes. All of the solid succinic acid, initially present, had dissolved and remained in solution after again reaching room temperature. Next, 133.07 g of methanol were added to the solution in the bottle, the bottle re-capped, and then shaken vigorously to thoroughly mix the resulting solution. The composition of the resulting solution was as follows:

| | |
|---|---|
| Succinic Acid | =20.35% (by wt.) |
| $NH_3$ | =5.88% (by wt.) |
| Methanol | =11.09% (by wt.) |
| $H_2O$ | =62.69% (by wt.) |

The approximate molar ratio of this feedstock solution is approximately as follows:

$NH_3$/Succinic Acid/Methanol/$H_2O$=2.0/1.0/2.0/20.2

This feedstock solution was used in examples 1, 2, 3, & 5 in Table 1 and also in examples 1&2 in Table 2.

Aqueous Feedstock Solution #2

101.74 g (0.862 mole) of succinic acid was weighed into a 500 ml poly bottle along with 271.22 g (15.055 moles) of DI water. The mixture was gently agitated to break up the lumps of solid succinic acid, and to try to wet all of the solid. Next, 99.48 g of concentrated ammonia solution (29.5% $NH_3$ by wt.) (1.723 moles $NH_3$ +3.893 moles $H_2O$) was added to the mixture in the bottle, the bottle re-capped, then shaken vigorously. After shaking, the bottle and its contents were cooled to room temperature. 27.60 g (0.861 mole) of methanol were added to the solution in the bottle, the bottle re-capped, then shaken to thoroughly mix the contents. The composition of the resulting solution was as follows:

| Succinic Acid | =20.35% (by wt.) |
|---|---|
| $NH_3$ | =5.87% (by wt.) |
| Methanol | =5.52% (by wt.) |
| $H_2O$ | =68.27% (by wt.) |

The approximate molar ratio of this feedstock solution was approximately as follows:

$NH_3$/Succinic Acid/Methanol/$H_2O$=2.0/1.0/1.0 22.0
This feedstock solution was used in example 4 in Table 1.

Aqueous Feedstock Solution #3

101.74 g (0.8615 mole) of succinic acid and 320.92 g (17.8138 moles) of DI water were weighed into a 500 ml poly bottle. The mixture was gently agitated to break up the lumps of solid succinic acid, and to try to wet all of the solid. Next, 49.74 g of concentrated ammonia solution (29.5% $NH_3$ by wt.) (0.861 moles $NH_3$+1.9465 moles $H_2O$) was added to the mixture in the bottle, the bottle re-capped, then shaken. After shaking, the bottle and its contents were cooled to room temperature. 27.60 g (0.861 mole) of methanol were then added to the solution in the bottle, the bottle re-capped, then shaken to thoroughly mix the contents. The composition of the resulting solution was as follows:

| Succinic Acid | =20.35% (by wt.) |
|---|---|
| $NH_3$ | =2.93% (by wt.) |
| Methanol | =5.52% (by wt.) |
| $H_2O$ | =71.20% (by wt.) |

The approximate molar ratio of this feedstock solution was approximately as follows:

$NH_3$/Succinic Acid/Methanol/$H_2O$=1.0/1.0/1.0/23.0
This feedstock solution was used in examples 6 & 7 in Table 1.

Aqueous Feedstock Solution #4

68.22 g (0.6031 mole) of N-methylsuccinimide (NMS) and 281.78 g (15.64 moles) of DI water were weighed into a 500 ml poly bottle. The bottle was re-capped then shaken vigorously for several minutes until all of the NMS appeared to have dissolved. The composition of the resulting solution was as follows:

| N-methysuccinimide | =19.49% (by wt.) |
|---|---|
| H2O | =80.51% (by wt.) |

The approximate molar ratio of this feedstock solution is approximately as follows:

N-methylsuccinimide/$H_2O$=1.0/25.9
This feedstock solution was used in examples 8, 9, 10 & 11 in Table 1.

Aqueous Feedstock Solution #5

85.37 g (0.8615 mole) of succinimide and 387.06 g (21.4852 moles) of DI water were weighed into a 500 ml poly bottle. Next, 27.60 g (0.8614 mole) of methanol was added to the mixture in the bottle, the bottle re-capped, then shaken vigorously. After shaking the bottle and its contents for ~15 minutes all but a small amount of the solid material appeared to have gone into solution (the amount of remaining undissolved solid material was probably less than ~0.2 g). The composition of the resulting solution was as follows:

| Succinimide | =17.07% (by wt.) |
|---|---|
| Methanol | =5.52% (by wt.) |
| $H_2O$ | =77.41% (by wt.) |

The approximate molar ratio of this feedstock solution was approximately as follows:

Succinimide/Methanol/$H_2O$=1.0/1.0/24.9
This feedstock solution was used in example 3 in Table 2.

Aqueous Feedstock Solution #6

85.37 g (0.8615 mole) of succinimide, 359.42 g (19.9509 moles) of DI water, and 55.21 g (1.7232 mole) of methanol were weighed into a 500 ml poly bottle. The bottle was then capped and the contents shaken vigorously for ~10 minutes. Undissolved material remained after that amount of time, so the capped bottle was held under hot running water for ~10 minutes (with occasional shaking). Even after holding under hot water for that amount of time, there still appeared to be ~0.1 g of undissolved white solid in the container. Upon cooling to room temperature, no additional white solid material appeared to fall out of solution. The composition of the resulting solution was as follows:

| Succinimide | =17.07% (by wt.) |
|---|---|
| Methanol | =11.04% (by wt.) |
| $H_2O$ | =71.88% (by wt.) |

The approximate molar ratio of this feedstock solution was approximately as follows:

Succinimide/Methanol/$H_2O$=1.0/2.0/23.2
This feedstock solution was used in examples 4 & 5 in Table 2.

Aqueous Feedstock Solution #7

106.71 g (1.0769 mole) of succinimide and 324.33 g (18.0031 moles) of DI water were weighed into a 500 ml poly bottle. The bottle was then capped and the contents shaken to dissolve the solid. It was necessary to heat up the contents of the bottle slightly by holding the bottle under hot running water. After heating the solution to ~37° C. almost all of the solid had dissolved. The cap was removed and 69.09 g (2.156 moles) of methanol was added to the mixture. The bottle was again re-capped and shaken to mix the contents, then allowed to cool to room temperature. A small amount of white solid fell out of solution upon cooling. Re-warming the solution (to ~40° C.) was found to be sufficient to re-dissolve the solids. The composition of the resulting solution was as follows:

| Succinimide | =21.34% (by wt.) |
|---|---|
| Methanol | =13.85% (by wt.) |
| $H_2O$ | =64.85% (by wt.) |

The approximate molar ratio of this feedstock solution is approximately as follows:

Succinimide/Methanol/$H_2O$=1.0/2.0/16.7

This feedstock solution was used in example 6 in Table 2.

Description of the Semi-Batch Reactor System

Examples 1–11 of Table 1 and examples 1–6 of Table 2 were conducted in a modified 450 ml Parr autoclave system constructed of Hastelloy® C. The system incorporated a sealed magnetically driven stirrer assembly, internal cooling loop, internal control thermocouple, 0–3000 psig pressure gauge, and filter-ended dip tube. The dip tube was used both for gas and liquid addition to the reactor vessel (but not simultaneously) and also for the removal of liquid product samples taken periodically during the runs. The reactor system was set up to run under a relatively fixed hydrogen or nitrogen pressure during the runs. This was accomplished by setting the gas cylinder delivery pressure to the desired run pressure (in advance of the run), then opening the vessel to the gas delivery system once the desired run temperature had been reached. The dip tube fitting had separate shutoff valves for the gas addition and liquid addition/removal. The shut off valve to the gas delivery system was closed prior to drawing out a liquid product sample. After sampling, the liquid shut off valve would be re-closed and the gas feed shutoff valve re-opened to the gas delivery system. A small change in the observed system pressure was usually encountered for the duration of the sampling period. The reactor vessel was electrically heated (Parr reactor heating jacket) and used a Parr temperature controller equipped with an integral tachometer and variable speed control. Times required for the initial heat up to run temperature were generally ~½ hour in duration.

Catalyst Pre-Treatment Procedures Used in Semi-Batch Reactor Run Examples
(Pyrrolidinone Synthesis Runs)

Prior to use, all of the catalyst preparations described herein, were activated by an appropriate chemical reduction procedure. For all of the examples given in this document the catalyst activation procedure is accomplished via hydrogen reduction at an appropriate temperature condition. For all of the semi-batch run examples, the catalyst pretreatments (hydrogen reductions) were conducted in the semi-batch reactor vessel (450 cc Parr autoclave), prior to the addition of the liquid feedstock solution. All of the catalysts used in examples 1–11 in Table 1 were Rh-based catalysts prepared on the same carbon support material, and therefore all of the catalyst preps used in those examples received identical catalyst pre-treatments ($H_2$ reductions). In all cases, the weight of the dried, un-reduced catalyst preparation was nominally 3.75 g which was placed into a clean, dry reactor body. The rest of the reactor was then assembled and connected to the gas feed system, the cooling water lines, the rupture disc line, the control thermocouple connector, and to the stirrer drive motor. Following pressure testing, the reactor vessel was purged with $N_2$ or Argon to insure that all of the residual air was removed from the vessel prior to the addition of hydrogen. After purging with either $N_2$ or Argon, the vessel is pressurized to 400 psig with whichever of the two inert gases were initially used. Next, 100 psig of additional hydrogen pressure is added to the reactor vessel and the vessel subsequently sealed off (reduction mixture was effectively a 20% $H_2$ in $N_2$ or Ar mixture). The internal stirrer is started and set at ~150 rpm to provide some internal mixing of the gasses inside the reactor vessel. Once the stirrer started, the reactor vessel was heated to 120° C., where the temperature was maintained for a period of 4 hours. At the end of the 4 hours, the temperature controller was turned off, and the reactor vessel allowed to cool to room temperature. The spent reduction gasses were then vented from the reactor and the reactor again purged with $N_2$ or Argon.

Aqueous Feedstock Solution Addition and Procedure used to Conduct Semi-Batch Reactor Run Examples (Pyrrolidinone Synthesis Runs)

The aqueous feedstock solution was added to the reactor vessel through the liquid addition/removal port on the reactor. Typically, ~150 cc of liquid feedstock solution was added to the reactor. After the liquid feedstock solution was added, the system was initially purged with hydrogen gas to remove air that may have gotten into the reactor vessel during the liquid addition. The vessel was pressurized to ~500 psig with $H_2$, and the gas inlet line to the reactor vessel closed. The internal stirrer was turned on and adjusted to ~500 rpm, then the system was heated up to the desired run temperature. When the reactor vessel reaches the desired run temperature, a sample of the liquid feedstock/product solution was removed from the reactor vessel, then the vessel was opened to the gas delivery system and the reactor pressure rose to the pre-set desired run pressure. The time when the reactor system was opened up to the gas delivery system is designated T=0 hrs., or the time that the run is considered to have been started. Periodic liquid product samples were withdrawn from the reactor vessel and analyzed to monitor the disappearance of starting materials and the formation of reaction products. Product samples are numbered according to how many hours had expired between the run start time and the time that a particular sample had been removed from the reactor. For instance, if the run start time for a particular reaction were 9:00 A.M. and a sample was withdrawn from the reactor at 10:30 A.M. (~1.5 hours after the run start time), then the sample would be designated as the T+1.5 hr. sample. The product samples were analyzed by gas chromatography and conversion and product selectivity data calculated for each catalyst and set of reaction conditions.

Description of NMS Synthesis Runs Conducted in the Semi-Batch Reactor System Examples 1–6 of Table 2 were all examples of the non-catalyzed, hydrothermal synthesis of NMS from either diammonium succinate/methanol or succinimide/methanol mixtures. The reactions were conducted at elevated temperatures using a nitrogen cover gas. In these runs, the feedstock solution (~150 ml) was generally added to the reactor vessel following the usual pressure testing procedure. After the liquid had been added to the reactor vessel, the vessel was purged with nitrogen, to remove any air that may have gotten into the vessel during the liquid feedstock addition. Next, the reactor vessel was pressurized with additional nitrogen gas (typically 600–1000 psig depending upon the final run temperature) then closed off to the pressurized gas delivery system. The internal stirrer was turned on and adjusted to ~500 rpm, then the system was heated up to the desired run temperature (either 265° C. or 300° C.). A sample of the feed/product solution would be taken when the setpoint temperature was reached, then the reactor vessel would be opened up to the pressurized gas delivery system (pre-set to either 1900 or 2200 psig of $N_2$ pressure). Periodic liquid product samples were withdrawn from the reactor vessel and analyzed to monitor the disappearance of starting materials and the formation of reaction products. The product samples were analyzed by gas chromatography and conversion and product selectivity data calculated for each catalyst and set of reaction conditions. Table 1 contains a summary of semi-batch reactor run results showing how the choice of catalyst, feedstock, and process conditions can affect reaction rates and product selectivities in the liquid phase synthesis of pyrrolidinones.

TABLE 1

Synthesis of NMP - Semibatch Process Results

| catalyst | Temp. (° C.) | Pressure (MPa) | Feedstck solution | Time, (hr) at max. | % Conv. yield | Max. Yield of NMP + 2-py (%) | NMP/2py mole ratio |
|---|---|---|---|---|---|---|---|
| 5% Rh/C | 265 | 13 | 1 | 21.0 | 98.5 | 83.3 | 1.58 |
| 2.5% Rh/2.5% Zr/C | 265 | 13 | 1 | 21.3 | 97.5 | 95.2 | 2.31 |
| 2.5% Rh/2.5% Re/C | 265 | 13 | 1 | 8.0 | 90.6 | 90.0 | 1.15 |
| 5% Rh/C | 265 | 13 | 2 | 5.0 | 95.5 | 80.7 | 0.55 |
| 2.5% Rh/2.5% Re/C | 200 | 13 | 1 | 24.0 | 93.5 | 47.2 | 0.21 |
| 5% Rh/C | 265 | 13 | 3 | 7.0 | 89.6 | 70.9 | 0.86 |
| 2.5% Rh/2.5% Zr/C | 200 | 13 | 3 | 23.5 | 80.4 | 24.8 | 0.16 |
| 5% Rh/C | 265 | 13 | 4 | 8.0 | 95.6 | 74.1 | 2.15 |
| 2.5% Rh/2.5% Re/C | 265 | 13 | 4 | 5.0 | 88.7 | 53.7 | 5.28 |
| 2.5% Rh/2.5% Zr/C | 200 | 13 | 4 | 24.0 | 93.5 | 81.1 | 38.1 |
| 2.5% Rh/2.5% Re/C | 200 | 13 | 4 | 8.0 | 94.8 | 88.8 | 67.3 |

All tests at 1900 psig (13.2 MPa)

As can be seen from the results in Table 1, increasing methanol increased the ratio of NMP. In a one-step reaction, better results may be obtained in a range of about 230 to 280° C. Higher N-alkyl (e.g. NMP) yields are obtained at an alcohol:compound B ratio of at least 2. Surprisingly, we discovered that a metal oxide-containing catalyst resulted in superior results (see, for example, Example 2). Also, unexpectedly, by hydrogenating a succinimide in the presence of a Pd or Rh catalyst, at a temperature less than about 220° C. for less than 10 hours, we found that compounds (C), preferably NMP, can be obtained in a yield of at least 80%.

TABLE 2

Synthesis of NMS

| Temp. (° C.) | Pressure (MPa) | Feedstock Solution | Time, (hr) at max. yield | Max. Yield of NMS (%) | % conversion |
|---|---|---|---|---|---|
| 265 | 13 | 1 | 3.0 | 66.9 | 100 |
| 300 | 13 | 1 | 3.5 | 83.3 | 100 |
| 265 | 13 | 5 | 4.0 | 43.2 | 75.3 |
| 300 | 13 | 6 | 2.5 | 82.3 | 97.8 |
| 300 | 15 | 6 | 3.0 | 79.0 | 99.1 |
| 300 | 13 | 7 | 0.5 | 87.5 | 89.0 |

As can be seen from Table 2, among other results, we discovered that surprisingly superior results are obtained from aqueous phase hydrogenations in which the molar ratio of compound B):water is at least about 0.06, in some preferred embodiments in a range of 0.06 to 0.2

Continuous Flow Reactor Run Examples:

Aqueous Feedstock Solutions used in Continuous Flow Reactor Run Examples

Aqueous Continuous Feedstock Solution #1

114.73 g (1.014 moles) of N-methylsuccinimide (Aldrich Chemical Co.) was weighed into a 1000 ml Erlenmeyer flask along with 474.01 g (26.312 moles) of deionized water. The contents of the flask were vigorously stirred until all of the soluble material had gone into solution. A small quantity (estimated to be less than 0.02 g) of black colored insoluble material remained suspended in the otherwise colorless solution. The black particles were removed by filtering. The composition of the resulting solution was as follows:

| N-methylsuccinimide | =19.49% (by wt.) |
|---|---|
| $H_2O$ | =80.51% (by wt.) |

The approximate molar ratio of this feedstock solution is approximately as follows:

N-methylsuccinimide/$H_2O$=0 1.0/25.9

Aqueous Continuous Feedstock Solution #2

200.00 g (1.768 moles) of N-methylsuccinimide (Aldrich Chemical Co.) was weighed into a 32 oz Nalgene® poly bottle along with 826.18 g (45.861 moles) of DI water. The bottle was capped and shaken vigorously until all of the solid material had dissolved. The composition of the resulting solution was as follows:

| N-methylsuccinimide | =19.49% (by wt.) |
|---|---|
| $H_2O$ | =80.51% (by wt.) |

The approximate molar ratio of this feedstock solution is approximately as follows:

N-methylsuccinimide/$H_2O$=1.0/25.9

Description of the Continuous Flow Reactor System

Examples 1–7 of Table 3 were generated in a small continuous flow reactor system configured as a trickle bed reactor. In this reactor configuration both gas and liquid feeds are introduced into the reactor in a co-current down-flow manner. The reactor tube itself is an Autoclave Engineers 316 SS medium pressure reactor tube (0.750" O.D. ×0.098" wall thickness with coned and threaded ends). An internal thermowell tube (3/16" O.D. heavy walled 316 SS tube welded shut on one end) runs from the bottom end up through the entire heated length of the reactor tube, so that the reactor's temperature profile can be probed. The reactor tube is jacketed by a 2" diameter×18" long heat exchanger through which hot oil is circulated to provide uniform heating of the reactor tube (catalyst is generally packed within the middle 14" of the 18" heated zone; bed temperatures can generally be maintained within +/−0.5° C.). The oil was heated and circulated by a Julabo closed system heated pump. Liquid feeds were supplied to the reactor by an ISCO high-pressure syringe pump, equipped with a syringe heating jacket and heated liquid delivery lines. The liquid delivery line and gas delivery line entered the reactor together via an Autoclave Engineers "tee" at the top end of the reactor tube. Feed gases were metered into the reactor using Brooks high-pressure mass flow controllers. The gas feeds to the mass flow controllers were provided by a manifolded gas delivery system at constant pressure. A dome-loaded back-pressure regulator was used to maintain the reactor at the desired system pressure. Gaseous and liquid products are separated in chilled collection vessels, where liquid products were periodically drawn off and analyzed. Gaseous materials were measured with a wet test meter, and gas samples were periodically withdrawn and analyzed by gas chromatography.

The catalyst used in the continuous flow reactor was made by an incipient wetness catalyst preparation technique. This was done by taking a 18.34 g sample of an Engelhard carbon (CTC=95%, incipient wetness of 0.76 cc/g) to prepare a 2.5% rhodium and 2.5% rhenium catalyst. The impregnation volume of this preparation was 13.9 ml. The amounts of rhodium and rhenium are specified as final weight percent of the reduced metal on the carbon support. Thus, the required weight of active metal precursor was back calculated to determine the necessary weight of rhodium nitrate and perrhenic acid. For this example, 0.48 g of rhodium metal was required, and thus 4.65 of rhodium nitrate stock solution was required (at 10.51% rhodium metal by weight). Also, 0.48 g of rhenium metal was required, and thus 0.93 g of perrhenic acid was required (at 52.09% rhenium metal by weight). 0.93 g of perrhenic acid and 4.67 g of rhodium nitrate was added to a graduated cylinder and stirred. The solution was then topped up to a final volume of 14 ml, stirred, and allowed to stand for 5 minutes. The solution was then added in 1 to 2 ml aliquots to the jar containing the 18.34 g of carbon. After each addition, the jar was capped and shaken until the carbon flowed freely in the vessel. Upon addition of the entire volume of solution, the carbon was sticky and slightly clumped. The carbon sat closed at room temperature with intermittent agitation for 3 hours and appeared dry and mostly granular, with some material still adhering to the walls of the jar. The support was then placed uncapped in a vacuum oven set to 100° C. and 20 inHg house vacuum and left to dry overnight. The catalyst was reduced prior to use.

The reactor body was packed with about 10 ml of crushed quartz followed by 0.5 cm of quartz wool. The 2.5% Rh/2.5% Re on Engelhard 95% CTC carbon catalyst was added in 10 ml increments, followed by light tamping to achieve uniform packing. Upon addition of 40 ml (18.31 g) of catalyst, the bed was capped with another 0.5 cm of quartz wool. The reactor was then assembled in the flow reactor test stand. The catalyst was first reduced at 120C for 16 hours under a cover gas of 4% hydrogen in argon at atmospheric pressure. Upon reduction, the cover gas was switched to hydrogen flowing at 18 SLPH and the pressure raised to 13 MPa while the column temperature was changed to the first operating point of 200° C. After equilibrating the temperature and gas flowrate, the liquid feed was added via high pressure Isco liquid pump at 100 ml/hr. From previous trickle bed experience, a total of 3 or more bed volumes of feed were allowed to pass through the reactor before it was considered equilibrated. Upon equilibration, approximately 20 to 30 ml of product was collected in a sample vial before the reactor conditions were adjusted and allowed to equilibrate again. During each sample period, a gas sample was taken from the low pressure side of the back pressure regulator and subjected to fixed gas analysis. The samples were immediately transferred to a refrigerator and batched for analysis on a GC. Prior to idling the reactor following a series of run conditions, approximately 3 bed volumes of deionized water was passed across the reactor, and the reactor was lowered to 100° C. and held at pressure under reducing conditions with a low flow of hydrogen until the next feed and series of run conditions. Results are shown in Table 3.

TABLE 3

Synthesis of NMP - Continuous Flow Reactor

| Feedstock | 1 | 1 | 1 | 2 | 2 | 2 | 2 |
|---|---|---|---|---|---|---|---|
| $H_2$ flow (slph) | 18.2 | 18.2 | 14.4 | 8.3 | 8.3 | 18.2 | 18.2 |
| $H_2$/NMS | 4.3 | 4.3 | 4.6 | 4.2 | 4.2 | 4.6 | 4.6 |
| psi | 1900 | 1900 | 1900 | 1900 | 1900 | 1900 | 1200 |
| Temp. (° C.) | 200 | 180 | 180 | 200 | 220 | 250 | 250 |
| feed (ml/hr) | 100 | 100 | 80 | 50 | 50 | 100 | 100 |
| conversion % | 93.6 | 78.0 | 85.3 | 98.7 | 99.4 | 97.8 | 88.2 |
| NMP selec. | 55.5 | 50.0 | 52.4 | 57.1 | 60.0 | 64.1 | 75.7 |
| 2-py selec. | 0.7 | 0.0 | 0.0 | 1.1 | 1.8 | 0.0 | 0.6 |

Hydrolysis Examples

A composite testing feedstock was prepared by combining products obtained from the continuous flow testing (columns 2 and 3 of Table 3). The analysis of this composite is shown in the Table 4. 56.18 g of this material was loaded into a 300 ml Parr autoclave, sealed, and the purged repeatedly with nitrogen. The autoclave was stirred at 500 rpm, and a cover gas of nitrogen was used to pressurize the autoclave to 4 MPa. The reactor heater was turned on to a set point of 250° C. After 30 minutes, the reactor achieved 250° C. and the pressure of nitrogen was increased to 9 MPa. The reactor was held at 250° C. and 9 MPa for 15.5 hours, after which it was quickly cooled and the sample removed for analysis. The results are shown in the table below:

TABLE 4

| Hydrolysis | | |
|---|---|---|
| | initial | final |
| % Succinimide | 0.05 | 0.00 |
| % N-Methylsuccinimide | 3.09 | 2.98 |
| % Methanol | 0.15 | 0.13 |
| % Gamma-Butyrolactone | 0.15 | 0.04 |

TABLE 4-continued

| | Hydrolysis | |
|---|---|---|
| | initial | final |
| % N-Methyl-2-Pyrrolidinone | 6.42 | 10.42 |
| % N-Butyl-2-Pyrrolidone | 0.02 | 0.03 |
| % 2-Pyrrolidinone | 0.00 | 0.00 |

As can be seen from the Table, hydrolysis treatment substantially increased yield of the desired product NMP.

A second hydrolysis experiment conducted for a shorter time (1.6 hr) with the product obtained from the run in column 5 of Table 3 collected from the continuous hydrogenation testing under the conditions of the first experiment showed no change in the NMP yield. The difference in the results between the first and second experimental runs was likely due to differences in hydrogenation conditions, although experimental error is also a possibility. The feedstock for the second hydrolysis experiment was obtained from a run at higher temperature and slower flow rate—conditions that may not produce a compound (C) precursor compound.

CLOSURE

While preferred embodiments of the present invention have been described., it will be apparent to those skilled in the art that many changes and modifications may be made without departing from the invention in its broader aspects. The appended claims are therefore intended to cover all such changes and modifications as fall within the true spirit and scope of the invention.

What is claimed:

1. A method of making a compound having the formula (C) below:

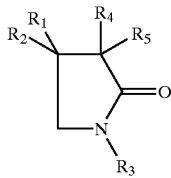

(C)

wherein $R_1$, $R_2$, $R_4$, and $R_5$ are, independently, H or a $C_1$ to $C_6$ alkyl or substituted alkyl; and wherein $R_3$ is H or a $C_1$ to $C_6$ alkyl or substituted alkyl; the method comprising reacting an initial compound with an alcohol and hydrogen in the presence of water and a catalyst, the initial compound having the formula (B) below:

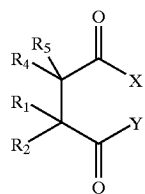

(B)

wherein $R_1$, $R_2$, $R_4$, and $R_5$ are, independently, H or a $C_1$ to $C_6$ alkyl or substituted alkyl, or wherein $R_2$ and $R_4$ together are replaced by a double bond; $R_3$ is H or a $C_1$ to $C_6$ alkyl or substituted alkyl; and X and Y are, independently, OH, O⁻, or where X and Y together are a bridging oxo; and wherein the catalyst comprises carbon, metal oxide and at least one metal selected from the group consisting of Pd, Rh, Pt, Ru, Ni and Co.

2. A method of producing a compound having formula (C) below:

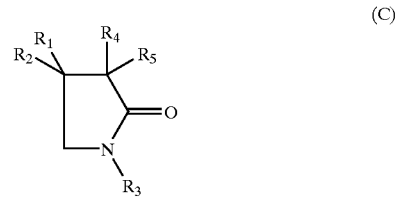

(C)

wherein $R_1$, $R_2$, $R_4$, and $R_5$ are, independently, H or a $C_1$ to $C_6$ alkyl or substituted alkyl; and wherein $R_3$ is H or a $C_1$ to $C_6$ alkyl or substituted alkyl, the method comprising:

a first step of reacting a compound of formula (B)

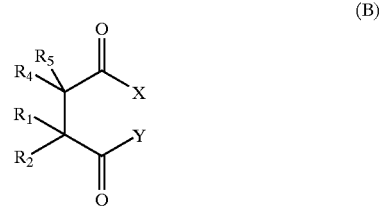

(B)

with ammonia in the presence of water, to form a compound of formula (A);

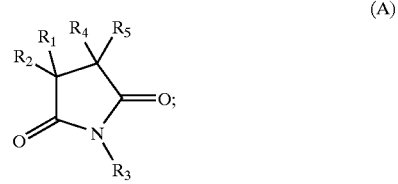

(A)

a second step of extracting the compound of formula (A) into an organic solvent; and a third step comprising hydrogenating the compound of formula (A) that was extracted in the second step in the presence of the catalyst.

3. The method of claim 1 wherein $R_1$, $R_2$, $R_4$, and $R_5$ are H.

4. The method of claim 3 wherein $R_3$ is H, methyl or ethyl.

5. The method of claim 1 further comprising providing ammonia during the reaction, wherein the catalyst comprises Re and at least one of Pd and Rh.

6. The method of claim 1 comprising the step of reacting a compound of formula (B) with ammonia in a molar ratio of ammonia to compound of formula (B) of 1 to 3, the alcohol being present at a molar ratio of alcohol relative to compound of formula (B) of at least about 2:1, wherein $R_3$ is $C_1$ to $C_6$ alkyl or substituted alkyl.

7. The method of claim 1 wherein the metal oxide contains at least 90% by mass of an oxide or oxides of one or more element selected from the group Zr, Ti, Hf, Ta, Nb, Mo and W.

8. The method of claim 7 wherein the metal oxide is 1 to 25 weight % of the total weight of the catalyst.

9. The method of claim 8 wherein the catalyst metal comprises from 0.1 to 10 weight percent of a dried form of the catalyst.

10. The method of claim 9, wherein hydrogen occurs in a reactor, and further comprising:
purifying the compound of formula (C) by distillation which leaves an undistilled residue;
hydrolyzing at least some of the residue to form hydrolyzed residue, and
recycling the hydrolyzed residue back to the reactor.

11. The method of claim 3, wherein $R_3$ is methyl, wherein hydrogenation occurs in a reactor and produces a product composition comprising N-methyl pyrrolidone (NMP), and further comprising:
removing at least one of hydrogen and the catalyst from the product composition;
removing at least a portion of the NMP from the product composition, leaving an NMP-depleted composition;
hydrolyzing the NMP-depleted composition to produce a hydrolyzed composition; and
a step comprising purifying NMP from the hydrolyzed composition or recycling the hydrolyzed composition to the reactor.

12. The method of claim 2 wherein the first step is conducted within a temperature range of 250 to 350° C.; wherein the second step is conducted at a temperature of less than 230° C., wherein the catalyst comprises one or more metals selected from the group consisting of Re, Rh, Pd, Pt, Ru, Ni, and Co, and wherein $R_3$ is methyl or ethyl.

13. The method of claim 12 wherein $R_3$ is methyl; wherein $R_1$, $R_2$, $R_4$, and $R_5$ are H; wherein the first step occurs in less than 1 hour; wherein the second step occurs in less than 1 hour; and wherein N-methyl pyrrolidone is obtained in a yield of at least 70%, based on the initial amount of the compound of formula (B).

14. The method of claim 13 further comprising, subsequent to said second step, a hydrolysis step in the absence of at least one of hydrogen and the catalyst.

15. The method of claim 2 wherein the compound of formula (A): is N-methyl succinimide and wherein the third step is conducted at a temperature of less than 220° C. and for a time of less than 10 hours; wherein N-methyl pyrrolidone is obtained in a yield of at least 80%, based on the initial amount of N-methyl succinimide.

16. The method of claim 3 wherein $R_3$ is methyl; wherein $R_1$, $R_2$, $R_4$, and $R_5$ are H; and further comprising:
obtaining a product mixture comprising a compound (C) precursor;
separating the compound (C) precursor from the catalyst, or from hydrogen, or from both the catalyst and hydrogen, to form a separated compound (C) precursor; and
hydrolyzing the separated compound (C) precursor.

17. The method of claim 1 wherein the metal oxide comprises at least one metal selected from the group consisting of Zr, Hf, Ta, Nb, Mo, W, Zn, Sn, V, Fe, U and Th.

18. A method of producing N-methyl pyrrolidone comprising:
providing a catalyst comprising a first metal, an oxide material comprising a second metal and a carbon support, the second metal comprising at least one member of the group consisting of Zr, Hf, Ta, Nb, Mo, W, Zn, Sn, V, Fe, U and Th; and
flowing an aqueous solution comprising succinimide over the catalyst in the presence of hydrogen to catalytically hydrogenate the succinimide, the hydrogenation forming N-methyl pyrrolidone and 2-pyrrolidone, a product ratio of N-methyl pyrrolidone to 2-pyrrolidone being greater than 5:1.

19. The method of claim 18 wherein the second metal further comprises a member of the group consisting of Si, Ti and Al.

20. The method of claim 18 wherein the first metal comprises Rh and the second metal comprises Zr.

21. The method of claim 18 wherein the catalyst contains from 0.1% to 10% of the first metal by weight.

22. The method of claim 18 wherein the catalyst comprises from 1% to 25% oxide material, by weight.

23. A method of forming a pyrrolidone compound comprising:
forming a solution comprising an initial compound having the formula below:

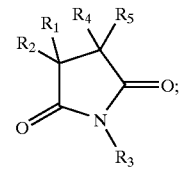

providing the solution into a reactor containing a catalyst comprising a metal oxide, the metal oxide having at least one metal selected from the group consisting of Zr, Hf, Ta, Nb, Mo, W, Zn, Sn, V, Fe, U and Th;
flowing hydrogen into the reactor; and
reacting the hydrogen with the initial compound in the presence of the catalyst, the reaction converting the initial compound into the pyrrolidone compound.

24. The method of claim 23 wherein the solution is an aqueous solution having a molar ratio of initial compound to water of about 1:25.9.

25. The method of claim 23 wherein the reactor is a continuous flow reactor and wherein the catalyst is a solid catalyst comprising a porous carbon support.

26. The method of claim 23 wherein $R_3$ is methyl.

27. The method of claim wherein $R_1$, $R_2$, $R_4$, and $R_5$ are all H.

* * * * *

UNITED STATES PATENT AND TRADEMARK OFFICE
CERTIFICATE OF CORRECTION

PATENT NO.    : 6,603,021 B2
DATED         : August 5, 2003
INVENTOR(S)   : Werpy et al.

It is certified that error appears in the above-identified patent and that said Letters Patent is hereby corrected as shown below:

Title page,
Item [57], ABSTRACT,
Line 2, delete "N-methylpyrrolidine" and insert -- N-methylpyrrolidone --.
Line 7, delete "N-methylpyrrolidine" and insert -- N-methylpyrrolidone --.

Column 3,
Line 38, delete "and".
Line 59, delete "N-methylpyrrolidine" and insert -- N-methylpyrrolidone --.

Column 4,
Line 43, delete "(alcohol  compound  B)" and insert -- (alcohol:compound B) --.

Column 9,
Line 42, delete "Rh(NO3)3" and insert -- $Rh(NO_3)_3$ --.

Column 10,
Line 3, delete "Before "0.8" insert -- ~ --.
Line 23, delete "Table__" and insert -- Table 1 --.

Column 11,
Line 23, delete "2.0/1.0/1.0 22.0" and insert -- 2.0/1.0/1.0/22.0 --.
Line 60, delete "N-methysuccinimide" and insert -- N-methylsuccinimide --.

Column 15,
Line 63, before "Aqueous" insert -- Preparation of --.

Column 16,
Line 36, delete "$H_2O$=0 1.0/25.9" and insert -- $H_2O$=1.0/25.9 --.

Column 17,
Line 2, delete "+/~" and insert -- +/- ~ --.

Column 18,
Line 49, delete "the" and insert -- then --.

UNITED STATES PATENT AND TRADEMARK OFFICE
CERTIFICATE OF CORRECTION

PATENT NO. : 6,603,021 B2
DATED : August 5, 2003
INVENTOR(S) : Werpy et al.

It is certified that error appears in the above-identified patent and that said Letters Patent is hereby corrected as shown below:

Column 22,
Line 52, after "claim" insert -- 23 --.

Signed and Sealed this

Second Day of November, 2004

JON W. DUDAS
*Director of the United States Patent and Trademark Office*